United States Patent [19]
Bernstein et al.

[11] Patent Number: 5,377,680
[45] Date of Patent: Jan. 3, 1995

[54] MRI CARDIAC IMAGE PRODUCED BY TEMPORAL DATA SHARING

[75] Inventors: Tsur Bernstein, Glendale; Thomas K. Foo, Waukesha, both of Wis.

[73] Assignee: General Electric Company, Milwaukee, Wis.

[21] Appl. No.: 102,166

[22] Filed: Aug. 4, 1993

[51] Int. Cl.$^6$ .............................................. A61B 5/055
[52] U.S. Cl. ................... 128/653.2; 128/696; 364/413.18
[58] Field of Search ............... 128/653.2, 653.1, 696; 324/309; 364/413.13, 413.18

[56] References Cited

U.S. PATENT DOCUMENTS

| | | | |
|---|---|---|---|
| 4,710,717 | 12/1987 | Pelc et al. | 128/653.2 |
| 4,903,704 | 2/1990 | Van Eggermond et al. | 128/653.2 |
| 4,911,149 | 10/1990 | Stokar | 128/653.2 |
| 4,961,426 | 10/1990 | Spraggins et al. | 128/653.2 |
| 4,979,512 | 12/1990 | Heubes | 128/653.2 |
| 5,068,609 | 11/1991 | Bruder et al. | 324/309 |
| 5,119,026 | 6/1992 | Iino et al. | 324/309 |
| 5,251,628 | 10/1993 | Foo | 128/653.2 |
| 5,281,916 | 1/1994 | Hinks et al. | 324/309 |

OTHER PUBLICATIONS

*Encoding Strategies for Three-Direction Phase-Contrast MR Imaging of Flow*, JMRI Jul./Aug. 1991, pp. 405–413, Pelc, et al.

*Cineangiography of the Heart in a Single Breath Hold with a Segmented TurboFLASH Sequence*, RSNA, Feb. 1991, pp. 357–360, Atkinson, et al.

MR Fluoroscopy: Technical Feasibility, *Magnetic Resonance in Medicine* 8, pp. 1–15, Jan. 25, 1988, S. J. Riederer, et al.

*Primary Examiner*—K. M. Pfaffle
*Attorney, Agent, or Firm*—Quarles & Brady

[57] ABSTRACT

Fast NMR pulse sequences are employed to acquire data sets from which a set of images can be reconstructed depicting a patient's heart at successive phases during the cardiac cycle. The number of images is increased by selecting views from adjacent data sets to form interpolated data sets that are employed to reconstruct images depicting the patient's heart at cardiac phases between the successive phases.

8 Claims, 2 Drawing Sheets

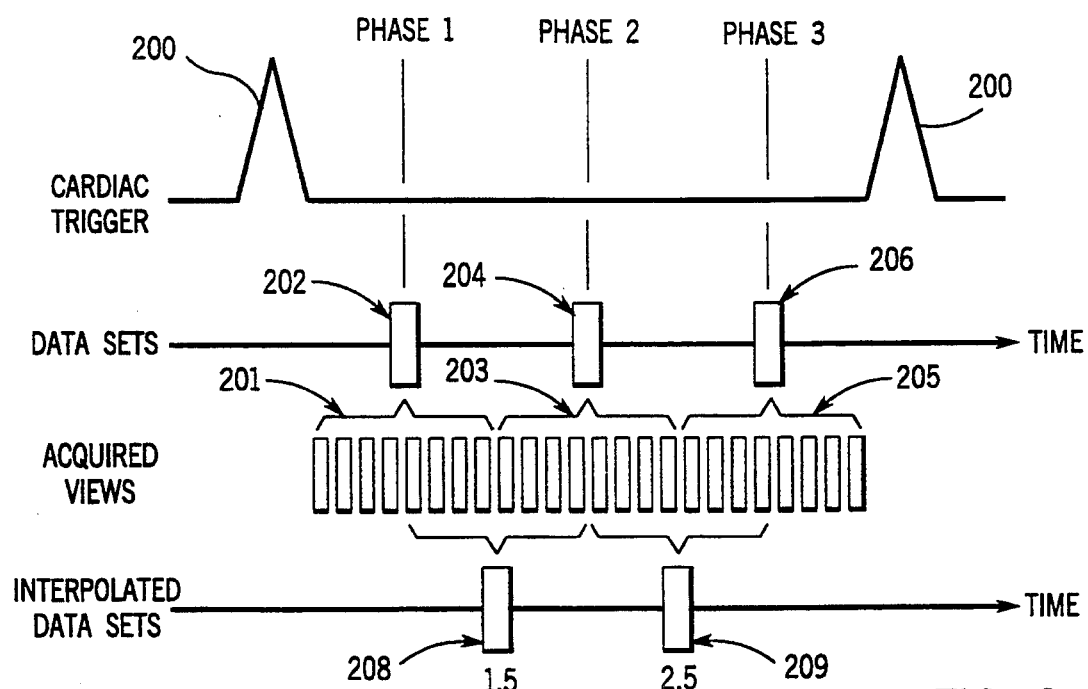
FIG. 2
FIG. 3
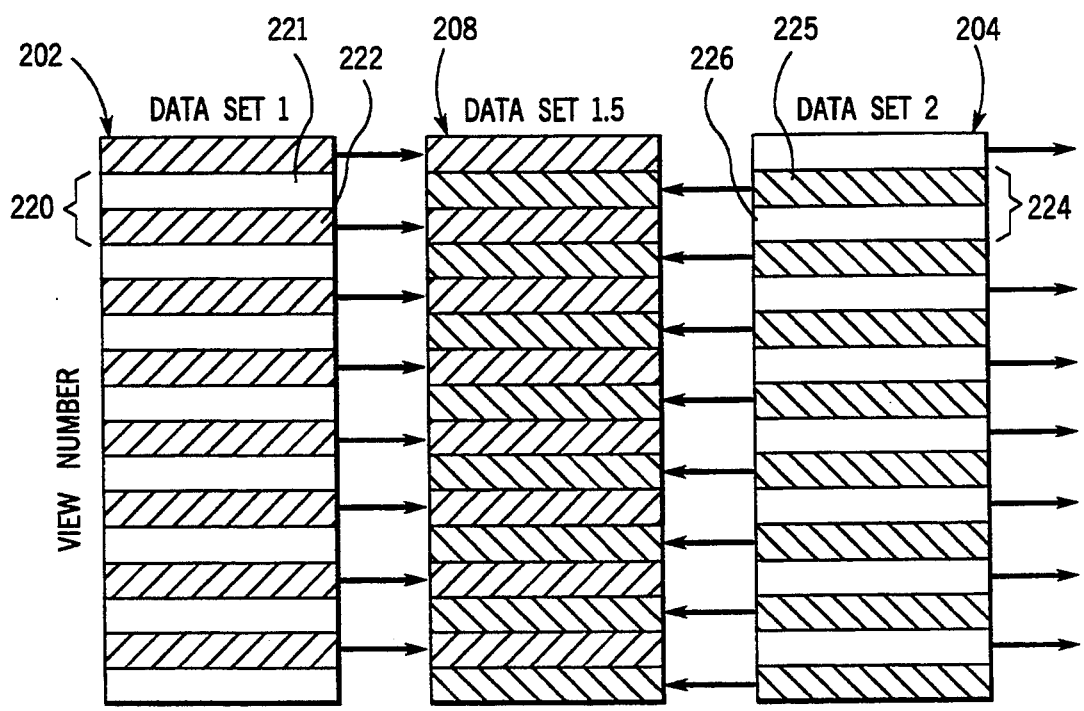

MRI CARDIAC IMAGE PRODUCED BY TEMPORAL DATA SHARING

BACKGROUND OF THE INVENTION

The field of the invention is nuclear magnetic resonance imaging methods and systems. More particularly, the invention relates to the production of temporal phase images in a fast, single breath-hold cardiac MRI acquisition.

When a substance such as human tissue is subjected to a uniform magnetic field (polarizing field $B_o$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Most NMR scans currently used to produce medical images require many minutes to acquire the necessary data. The reduction of this scan time is an important consideration, since reduced scan time increases patient throughput, improves patient comfort, and improves image quality by reducing motion artifacts. There is a class of pulse sequences which have a very short repetition time (TR) and result in complete scans which can be conducted in seconds rather than minutes. When applied to cardiac imaging, for example, a complete scan from which a series of images showing the heart at different phases of its cycle can be acquired in a single breath-hold.

The number of cardiac phase images that can be acquired during a scan is determined by a number of factors such as pulse sequence repetition time, the number of views acquired at each cardiac trigger and the patient's heart rate. By decreasing the number of views acquired at each cardiac trigger, more phase images can be acquired and the "temporal resolution" of the series of cardiac images is increased. However, total scan time is increased as the number of views acquired per cardiac trigger is reduced and the number of cardiac triggers required to complete acquisition of an image with the same spatial resolution increases.

SUMMARY OF THE INVENTION

The present invention is a method for nearly doubling the number of cardiac phase images that can be acquired during a scan with a given pulse sequence and within a single breath-hold. More specifically, the present invention includes producing a cardiac signal which indicates the patient's cardiac cycle; acquiring a plurality of NMR data sets from which images are reconstructed that depict the heart at a corresponding succession of phases in the cardiac cycle; producing an intermediate NMR data set by combining NMR data selected from two temporally adjacent NMR data sets; and reconstructing an image from the intermediate NMR data set which depicts the heart at a cardiac phase between the phases depicted by the temporally adjacent NMR data sets.

An object of the invention is to improve the temporal resolution of a series of cardiac images without increasing the total scan time. Without acquiring any additional NMR data, the present invention enables one to nearly double the number of cardiac images that can be reconstructed. Specifically, if n data sets are acquired during the scan, n−1 intermediate NMR data sets can be formed and a total of 2n−1 images can be reconstructed. The intermediate images depict the heart midway between the acquired phases to effectively double the temporal resolution. This is important to visualize cardiac states which persist for very short intervals, such as end-systole, which may be averaged out with rapid cardiac motion if the interval between images is too long.

BRIEF DESCRIPTION OF THE DRAWINGS

FIG. 2 is a graphic representation of the data acquisition sequence according to the present invention; and FIG. 3 is a schematic representation of how an interpolated image data set is formed from data acquired with the data acquisition sequence of FIG. 2.

DESCRIPTION OF THE PREFERRED EMBODIMENT

Figure 1:
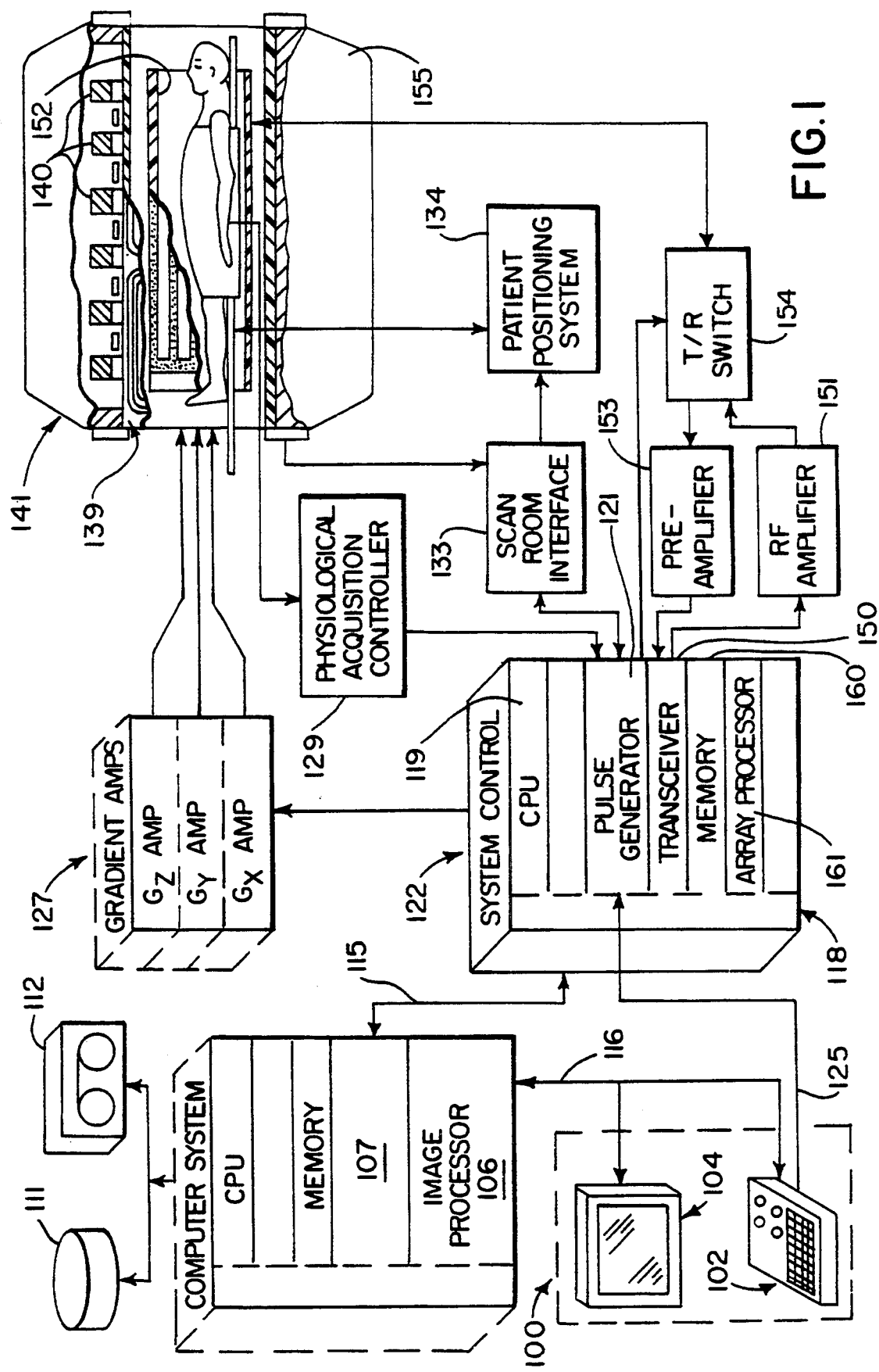
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104. For a more detailed description of the transceiver 150, reference is made to U.S. Pat. Nos. 4,952,877 and 4,992,736 which are incorporated herein by reference.

Referring particularly to FIG. 2, the cardiac acquisition in accordance with the preferred embodiment employs a series of fast gradient echo pulse sequences, with the repetition time, TR, of each gradient echo pulse sequence of between 6 and 15 ms, depending on the type of gradient hardware available and imaging parameters chosen. These pulse sequences are executed during the interval between the cardiac trigger signals 200 referred to as the R—R interval. The length of the R—R interval is a function of the patient's heart rate.

In a fast cardiac acquisition using gradient echoes, the R—R interval is divided up into many short segments, with each segment being a fast gradient acquisition pulse sequence with a nominal flip angle of between 20°–30°. Each fast gradient echo segment acquires an NMR signal representing a single line of k-space which is sometimes referred to as a view. Adjacent fast gradient echo segments are further combined into groups of 8 where the data from each group contributes to generating an image at different temporal phases of the cardiac cycle (R—R interval). The temporal location of these phase images depends on the relative time from the cardiac trigger (R-wave) 200 to the center of each group of fast gradient echo segments. In FIG. 2, the first group of 8 segments form the group 201 which acquires views for a first k-space data set 202. The next group of 8 fast gradient echo segments form another group 203 which acquires views at a second cardiac phase for a second k-space data set 204, and a third group of 8 segments form another group 205 which acquires views for a third k-space data set 206. Each group of fast gradient echo segments may employ contrast enhancement such as that disclosed in copending U.S. patent application Ser. No. 955,097, filed on Oct. 1, 1992 and entitled "Fast NMR Image Acquisition With Spectrally Selective Inversion Pulses", which is incorporated herein by reference.

The number of cardiac phases imaged during an acquisition depends on the number of groups of 8 segments which can fit into the patient's R—R interval. Eight fast gradient echo segments are nominally chosen to constitute a group as this provides a compromise between the temporal resolution of each image (defined as the time needed to acquire data from a group of 8 segments), and the total image acquisition time. As 128 views are nominally required to form a complete image, using 8 segments per group means that 8 views of k-space are acquired per cardiac trigger. Hence, 16 cardiac triggers are needed to complete the data acquisition, a time which is within the ability of most patients to maintain a breath-hold.

In the preferred embodiment, k-space is traversed in a sequential strip fashion during the scan. That is, views −60 through −53 are acquired on the first cardiac trigger, views −52 through −45 on the next cardiac trigger, and so forth. The last cardiac trigger picks up views −64 through −61 and views +60 through +63. This view order is preferred as it provides minimal image artifacts and also allows the central 8 low spatial frequency views to be acquired during a single R—R interval so that image artifacts resulting from inconsistencies between cardiac triggers are minimized. Another advantage of this sequential strip view order is that views may be shared between groups with minimal image artifacts. Significant discontinuity between k-space views are reduced in the shared data set and the central 8 views in the shared data set are still acquired during the same R—R interval as will become apparent below.

After 16 heart beats all 128 views are acquired for each data set 202, 204 and 206. Each k-space data set 202, 204 and 206 is then employed to reconstruct an image by performing a two-dimensional Fourier transformation as is well known to those skilled in the art. The resulting images depict the heart at three successive phases of the cardiac cycle, labelled phase 1, phase 2 and phase 3 in FIG. 2. In other words, the images are an effective time average of the cardiac motion during the time interval during which their views are acquired.

The present invention increases the number of separate cardiac phase images that can be reconstructed from the acquired k-space data sets. This is accomplished by forming intermediate k-space data sets by combining selected k-space views from the temporally adjacent k-space data sets. As shown in FIG. 2, a first intermediate data set 208 is formed by combining four views from the first segment 201 with four views from the second segment 203. The temporal average of these eight combined views is midway between cardiac phases 1 and 2, and the image reconstructed from intermediate data set 208 depicts the heart at a position midway therebetween. This is labelled phase 1.5 in FIG. 2. A similar intermediate data set 209 can be produced using eight views from the respective second and third segments 203 and 205, and an image is reconstructed depicting the heart midway between phases 2 and 3. This is labelled phase 2.5.

Referring particularly to FIGS. 2 and 3, the intermediate data set is comprised of NMR data from both temporally adjacent k-space data sets. As shown in FIG. 2, this data is acquired equally from both adjacent k-space data sets and the views closest in time to the desired temporal average are selected. As shown best in FIG. 3, the first k-space data set 202 can be represented as a succession of views ranging from view number $-64$, through zero, to view number $+63$. As explained above, eight of these views are acquired as a group during each cardiac cycle, and all 128 views are acquired, therefore, in 16 successive cardiac cycles. One such group of eight views is shown in FIG. 3, for example, at 220 with the first four views indicated by band 221 and the second four views indicated by cross hatched band 222. The second k-space data set 204 is acquired in the same fashion, but at a later cardiac phase. The same k-space group of eight views is indicated at 224, with the first four views indicated as cross hatched band 225 and the last four views indicated as band 226. The intermediate k-space data set 208 is formed by combining interleaved bands of views from the temporally adjacent data set 202 and 204 as shown. The eight view groups corresponding in k-space to the groups 220 and 224 is thus formed in the intermediate k-space data set 208 by combining the four view band 225 from data set 204 with the four view band 222 from data set 202. The number of views in each interleaved band can be varied, but the interleaving of four view bands in the preferred embodiment provides best results when eight view segments are acquired.

In the preferred embodiment the views are acquired in groups of eight starting at $-60$ and progressing through k-space to view $+59$. During the last cardiac cycle the bottom four views and the top four k-space views are acquired. As shown in FIG. 3, the top four views are combined in the subsequent intermediate k-space data set, whereas the bottom four views are combined in the temporally earlier intermediate k-space data set.

It should be apparent to those skilled in the art that many variations are possible from the preferred embodiment without departing from the spirit of the invention. For example, the number (n) of k-space data sets acquired during each cardiac cycle can vary and the number $(n-1)$ of intermediate k-space data sets will vary accordingly. Other fast pulse sequences can be used to acquire each view and the view order and combining scheme can be altered. In addition, the invention may be employed with either retrospective or prospective cardiac gating, although prospective gating with continuous RF excitation is preferred.

We claim:

1. A method for increasing the number of temporal cardiac phase images of a patient's heart from NMR data acquired synchrononsly during a succession of cardiac cycles, the steps comprising:
    a) producing a cardiac signal which indicates phase of the patient's heart during each cardiac cycle;
    b) acquiring first NMR data at a first cardiac phase during each of said succession of cardiac cycles and storing said first NMR data to form a first data set;
    c) acquiring second NMR data at a second cardiac phase during each of said succession of cardiac cycles and storing said second NMR data to form a second data set;
    d) reconstructing a first image from said first data set depicting the patient's heart at said first cardiac phase;
    e) reconstructing a second image from said second data set depicting the patient's heart at said second cardiac phase;
    f) selecting NMR data from said first and second data sets to form an intermediate data set; and
    g) reconstructing an intermediate image from said intermediate data set which depicts the patient's heart at a selected cardiac phase between said first and second cardiac phases.

2. The method as recited in claim 1 in which the images are reconstructed by performing a Fourier transformation on the first, second, and intermediate data sets.

3. The method as recited in claim 1 in which NMR data is selected equally from said first and second data sets to form the intermediate data set and the intermediate image depicts the patient's heart at a cardiac phase midway between said first and second cardiac phases.

4. The method as recited in claim 1 in which the first data set and second data set are each comprised of a plurality of successive views in which each view represents an acquired NMR signal at a selected phase encoding value, and the intermediate data set is comprised of a plurality of successive views in which some views are selected from said first data set and some views are selected from said second data set.

5. The method as recited in claim 4 in which the intermediate data set is formed by interleaving views from one of said first or second data sets with views from the other of said first or second data sets.

6. The method as recited in claim 4 in which two or more views of NMR data are acquired at each of said first and second cardiac phases during each of said cardiac cycles.

7. The method as recited in claim 6 in which the intermediate data set is formed from views in said first and second data sets which are acquired temporally adjacent to each other.

8. The method as recited in claim 1 which includes:
    acquiring additional NMR data at additional cardiac phases during each of said succession of cardiac cycles and storing said additional NMR data to form corresponding additional data sets and to thereby form a total of n data sets from NMR data acquired at n different cardiac phases; and
    step g) is performed $n-1$ times to reconstruct $n-1$ intermediate images from the n data sets.

* * * * *